United States Patent [19]

Serola

[11] Patent Number: 4,969,222
[45] Date of Patent: Nov. 13, 1990

[54] CONTOURED SUPPORT PILLOW

[76] Inventor: Richard J. Serola, 6600 Kalanianaole Highway, Suite 208, Honolulu, Hi. 96825

[21] Appl. No.: 540,142

[22] Filed: Jun. 19, 1990

[51] Int. Cl.$^5$ .................. A47G 9/00; A47C 20/00
[52] U.S. Cl. ...................................... 5/431; 5/436
[58] Field of Search ............ 5/431, 434, 436, 441, 5/446; 120/68, 69, 75

[56] References Cited

U.S. PATENT DOCUMENTS

| | | | |
|---|---|---|---|
| 1,231,839 | 7/1917 | Berlin | 5/431 |
| 1,869,460 | 8/1932 | Brand | 5/431 X |
| 2,521,780 | 9/1950 | Dodd | 5/441 |
| 2,839,766 | 6/1950 | Hull | 5/431 X |
| 3,003,815 | 10/1961 | Zinn | 5/436 |
| 3,009,172 | 11/1961 | Eidam | 5/436 |
| 3,747,916 | 7/1973 | Benson | 5/435 X |
| 4,908,892 | 3/1990 | Michelson | 5/431 |

*Primary Examiner*—Michael F. Trettel
*Attorney, Agent, or Firm*—Warren F. B. Lindsley

[57] ABSTRACT

A pillow for supporting the chest and shoulders of a patient when lying in a prone position with said pillow comprising a rectangular base having one end extending arcuately upwardly and over the base to form a narrow elongated rectangular shaped ridge top. The other end of the ridge extends downwardly from the top of the pillow and inwardly of its base to a second end of the pillow which connects the ridge of the pillow to its base.

7 Claims, 1 Drawing Sheet

CONTOURED SUPPORT PILLOW

BACKGROUND OF THE INVENTION

Numerous devices have been developed for supporting the peripheral portions of the body for a human when reclining, especially when attempting to relieve stresses on particular portions of the skeletal frame. Those afflicted with periodic back discomfort find relief in position changes which reorient the stress pattern on the skeletal frame relieving the soreness of the troublesome areas. To aid in reorienting the stress pattern a new and improved pillow is needed, especially one that relieves the stress in the upper and mid back brought about by anteriority of the thoracic vertebrae.

Anterior thoracic vertebrae are extremely common in our society because of the posture that we assume in our daily activities, namely raising our heads. When a person bends forward and raises his or her head the upper and middle thoracic vertebrae move anteriorly. When this happens on a consistant basis, the muscles and eventually the connective tissue accomodate and maintain this forward position.

In their normal position, the upper vertebrae and ribs of a human fit and function well together. As they are forced anterior, the ribs come closer together, compressing the space between them. This compression is transferred to the tissues and nerves. As this becomes chronic, a feeling of stress develops as the muscles tighten in reaction to the strain placed upon them. The muscles contract and maintain the anteriority even when the head is returned to its normal position.

Years of this chronic posture may compress the tissues to the point that the ribs cannot maintain their respective distances from each other. As they all try to fit into a smaller and tighter space, one or more become displaced backwardly. This causes rotation of the vertebrae, increased pressure on the nerves and tissues, increased muscle pain, decreased circulation, increased muscle spasm, and a chronic spasm cycle which further increases the pressure on the nerves and tissues.

People who suffer most from this condition are those who do overhead work, who sit at a desk and do paperwork, typists, mechanics, construction workers, chiropractors, and massage therapists, i.e., anyone who raises his or her head for a prolonged time.

Therefore, a need exists for a particular pillow that relieves this anterior thoracic condition by reversing the pressure on the rib cage.

DESCRIPTION OF THE PRIOR ART

The only known prior art is the elongated cylindrically shaped pillow shown in FIG. 1 of the drawing.

SUMMARY OF THE INVENTION

In accordance with the invention claimed, an improved elongated conformed pillow is provided that supports the upper torso of the body in a given manner to relieve stress in the upper and mid back portions of the body brought about by anteriority of the thoracic vertebrae.

It is, therefore, one object of this invention to provide a new and improved contoured pillow for supporting the head and shoulders of a user in a given manner to relieve anterior thoracic compression.

Another object of this invention is to provide a specially contoured supporting pillow that fits comfortably between the breasts of a female when lying in a prone position on the pillow.

A further object of this invention is to provide an inflatable pillow specially contoured to be placed under the chest of a user in a prone position such that the user's face clears the pillow supporting surface.

Other objects and advantages of the invention will become apparent from the following description when considered in conjunction with the accompanying drawing.

BRIEF DESCRIPTION OF THE DRAWING

The present invention may be readily described by reference to the accompanying drawing, in which.

DESCRIPTION OF THE PREFERRED EMBODIMENT

Figure 1:
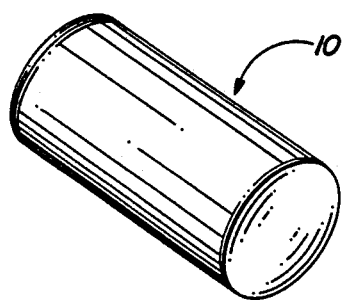
FIG. 1 is a perspective view of an elongated cylindrical foam filled pillow forming a part of the prior art.

Referring more particularly to the drawing by characters of reference, FIG. 1 illustrates a resilient cylindrically shaped pillow 10 forming the closest known prior art. This pillow filled with a soft foam like material must be used on a supporting surface which permits the face of a user or patient to clear its surface. This can only occur when it is used on the edge of a table so that the patient's face can hang over the table or the table has a hole in it for receiving the face of a patent.

Although it is possible to hang the user's head over the edge of a table while using the prior art, this action causes excess blood to rush to one's head and could lead to increased cerebral blood pressure. It is, therefore, not recommended. Therefore, the only reasonable use of the prior art is with a specially made table with a hole for the face. This necessity prevents the average person from applying home treatment.

Figure 2:
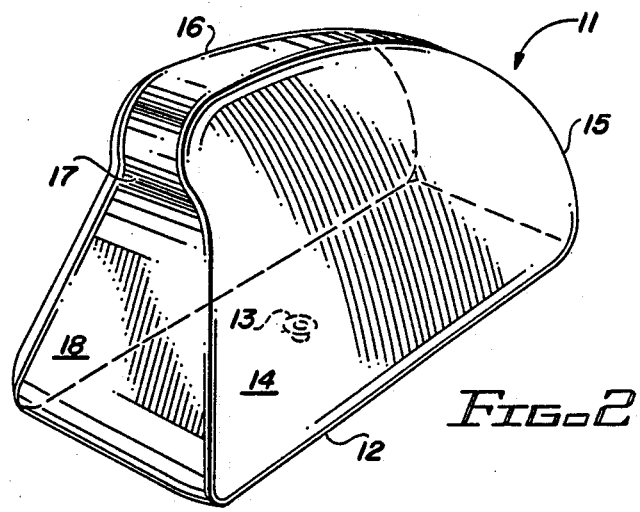
FIG. 2 is a perspective view of a contoured pillow embodying the invention.
Figure 3:
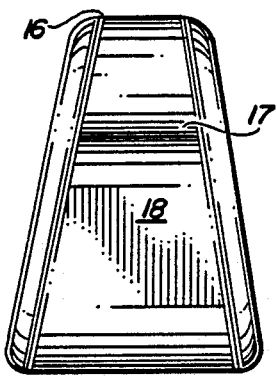
FIG. 3 is a left end view of FIG. 2.
Figure 4:
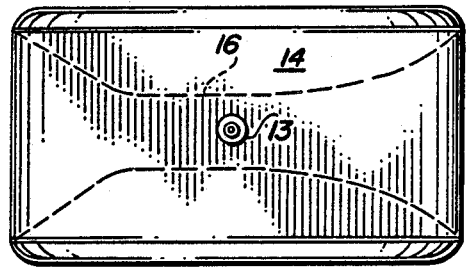
FIG. 4 is a bottom view of FIG. 2.

FIG. 2 discloses a new and improved contoured hollow inflatable pillow 11 formed of a suitable non pervious flexible material 12 such as for example, plastic. The pillow when inflated with air through a suitable valve 13 in its base 14 forms a contoured configuration the base of which assumes a rectangular flat shape with the right end of the pillow, as shown in FIG. 2, forming an arcuate configuration 15 that curves over the base tapering into a narrow ridge 16. This ridge extends to the left end of the pillow where it then extends downwardly toward base 14 and back on itself to form a slight indentation 17. From indentation 17, the left end flares outwardly in a trapezoidal configuration 18 to the left end of base 14.

Thus, when inflated the pillow forms the geometrical configuration shown in FIG. 2. It should be noted that this pillow may be filled with any suitable resilient material such as, for example, foam and still fall within the scope of this invention.

IN USE

Figure 5:
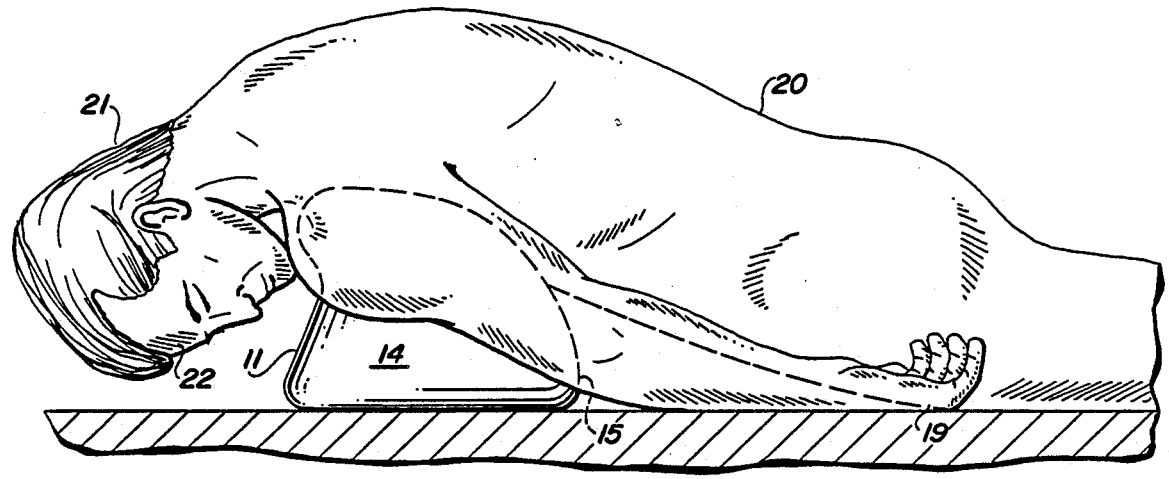
FIG. 5 is a perspective view of a user lying prone on the pillow shown in FIGS. 2–5.

When pillow 11 is properly inflated or filled with a suitable resilient foam like material, it may be placed on any suitable flat surface 19 with its base 14 resting on surface 19 and ridge 16 and contoured arcuate end 15 forming a supporting surface for the chest and stomach of a patient 20, as shown in FIG. 5. The head 21 of the patient extends over the trapezoidal configuration 18 of the pillow as shown.

As noted, face 22 of the patient clears surface 19 without undue distortion of the neck of the patient.

As shown in FIG. 5, pillow 11 is placed under the chest of the patient as high as it can be positioned without interference with his or her neck. The head 21 of the patient may hang downwardly as shown or the forehead of the patient may rest on surface 19. If the forehead does not reach surface 19 and is uncomfortable, as shown in FIG. 5, the patient may place a rolled towel or some other article under his or her forehead. It is important to keep one's head straight so that the vertebrae and ribs are in a normal position.

Pillow 11 causes the rib cage of the user to act as a spring with pressure on the chest of the user being relayed through the ribs to the back of the user at the points where the ribs are attached to the vertebrae. This spring like action slowly opens the rib cage, decompresses the tissues, relaxes the muscles and returns the curve of the backbone toward its normal position.

Anterior thoracic compression in a patient has long been a very stubborn and difficult problem to correct on a permanent basis for the medical profession since the position that the patient assumes daily causes it to reoccur. The pillow disclosed and claimed herein provides the patient with a means for treatment at home to keep this chronic syndrome under control. Five minutes a day has been found to be an ideal time to use the disclosed pillow. Excess time on this pillow may lead to irritation of the rib-sternal articulations.

Caution should be observed. Pillow 11 is not recommended for people with heart, artery, lung or bone weakening diseases or with fractures of the bones of the neck or back. It is recommended that people over 60 years of age consult a doctor before using it.

It is believed that a large majority of people can benefit greatly from this simple but effective stress reliever.

Although but one embodiment of the invention has been illustrated and described, it will be apparent to those skilled in the art that various changes and modifications may be made therein without departing from the spirit of the invention or from the scope of the appended claims.

What is claimed is:

1. A supporting pillow for engaging the chest and shoulders of a user when lying in a prone position on the pillow, said pillow comprising:
   a substantially flat rectangular base having opposed ends,
   an arcuate shaped first end extending from one end of said base over the base at a predetermined distance therefrom and terminating at one end in a narrow rectangular ridge forming the top of said pillow,
   said ridge extending over the top of said pillow terminating in a second end generally directly over the other end of said base, and
   a second end of said pillow extending from said second end of said ridge in an outwardly extending manner to said other end of said base.
2. The supporting pillow set forth in claim 1 wherein: said second end of said pillow comprising a trapezoidal shaped configuration.
3. The supporting pillow set forth in claim 1 wherein: the width of said ridge is narrow enough to fit longitudinally of the user between his or her breasts.
4. The supporting pillow set forth in claim 1 wherein: said pillow is formed of a non-pervious material that is inflatable through a valve formed in said base.
5. The supporting pillow set forth in claim 1 wherein: said pillow is filled with a resilient material.
6. The supporting pillow set forth in claim 1 wherein: the second end of said ridge extends over and part way down said second end of said pillow.
7. The supporting pillow set forth in claim 1 wherein: the second end of said ridge extends over said second end of said pillow inwardly of said base to form a notch part way down said second end of said pillow.

* * * * *